US00PP18513P2

(12) United States Plant Patent
Wood

(10) Patent No.: US PP18,513 P2
(45) Date of Patent: Feb. 26, 2008

(54) *WEIGELA* PLANT NAMED 'BRAMWELL'

(50) Latin Name: *Weigela florida*
Varietal Denomination: Bramwell

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 11/518,608

(22) Filed: Sep. 8, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Weigela* plant named 'Bramwell', characterized by its compact and uniform plant habit; mounding growth habit; freely branching habit; grayed purple-colored stems; relatively small dark grayed purple-colored leaves; and long-lasting dark pink flowers.

1 Drawing Sheet

Botanical designation: *Weigela florida.*
Cultivar denomination: 'Bramwell'.

BACKGROUND OF THE INVENTION

The present invention relates to a new and distinct cultivar of *Weigela* plant, botanically known as *Weigela florida,* and hereinafter referred to by the name 'Bramwell'.

The new *Weigela* is a product of a planned breeding program conducted by the Inventor in Grand Haven, Mich. The objective of the breeding program was to develop new *Weigelas* with dark leaf color, uniform plant habit and hardiness.

The new *Weigela* originated from a self-pollination made by the Inventor during the spring of 1998 of the *Weigela florida* cultivar Alexandra, disclosed in U.S. Plant Pat. No. 10,772. The cultivar Bramwell was discovered and selected by the Inventor during the summer of 2000 as a flowering plant within the progeny of the stated self-pollination in a controlled environment in Grand Haven, Mich. Asexual reproduction of the new cultivar by cuttings in Grand Haven, Mich. since 2000 has shown that the unique features of this new *Weigela* plant are stable and reproduced true to type in successive generations of asexual reproduction.

SUMMARY OF THE INVENTION

The following traits have been repeatedly observed and are determined to be the unique characteristics of 'Bramwell'. These characteristics in combination distinguish 'Bramwell' as a new and distinct cultivar of *Weigela:*

1. Compact and uniform plant habit; mounding growth habit.
2. Freely branching habit.
3. Grayed purple-colored stems.
4. Relatively small dark grayed purple-colored leaves.
5. Long-lasting dark pink flowers.

In side-by-side comparisons in Grand Haven, Mich., under commercial practice, plants of the new *Weigela* differed from plants of the parent, the cultivar Alexandra, in the following characteristics:

1. Plants of the new *Weigela* were more compact and mounding than plants of the cultivar Alexandra.
2. Plants of the new *Weigela* are more freely branching than plants of the cultivar Alexandra.
3. Plants of the new *Weigela* had grayed purple-colored young stems whereas plants of the cultivar Alexandra had green-colored young stems.
4. Plants of the new *Weigela* had smaller and darker-colored leaves than plants of the cultivar Alexandra.
5. Plants of the new *Weigela* were hardier than plants of the cultivar Alexandra.

Plants of the new *Weigela* can be compared to plants of the *Weigela florida* cultivar Ruby Queen, disclosed in U.S. Plant Pat. No. 12,632. In side-by-side comparisons in Grand Haven, Mich., plants of the new *Weigela* differed from plants of the cultivar Ruby Queen in the following characteristics:

1. Plants of the new *Weigela* are more uniform and fuller than plants of the cultivar Ruby Queen.
2. Plants of the new *Weigela* were hardier than plants of the cultivar Ruby Queen.

Plants of the new *Weigela* can also be compared to plants of the *Weigela florida* cultivar Java Red, not patented. In side-by-side comparisons in Grand Haven, Mich., plants of the new *Weigela* differed from plants of the cultivar Java Red in the following characteristics:

1. Plants of the new *Weigela* were fuller and denser than plants of the cultivar Java Red.
2. Plants of the new *Weigela* had darker-colored leaves than plants of the cultivar Java Red.
3. Plants of the new *Weigela* had more vibrant pink-colored flowers than plants of the cultivar Java Red.

BRIEF DESCRIPTION OF THE PHOTOGRAPHS

The accompanying colored photographs illustrate the overall appearance of the new *Weigela,* showing the colors as true as it is reasonably possible to obtain in colored reproductions of this type. Colors in the photographs may differ slightly from the color values cited in the detailed botanical description which accurately describe the colors of the new *Weigela.*

The photograph at the top of the sheet comprises a side perspective view or a typical plant of the cultivar Bramwell.

The photograph at the bottom of the sheet is a close-up view of typical flowers and leaves of the cultivar Bramwell.

DETAILED BOTANICAL DESCRIPTION

The new *Weigela* has not been observed under all possible environmental conditions. The phenotype may vary somewhat with variations in environment such as temperature and light intensity, without, however, any variance in genotype. The aforementioned photographs, following observations and measurements describe plants grown during the spring in Grand Haven, Mich., in a polyethylene-covered greenhouse and under commercial production practices. Plants were about three years old when the photographs and description were taken. In the following description, color references are made to The Royal Horticultural Society Colour Chart, 1995 Edition, except where general terms of ordinary dictionary significance are used.

Botanical classification: *Weigela florida* cultivar Bramwell.

Parentage:

*Female or seed, parent.*—*Weigela florida* cultivar Alexandra, disclosed in U.S. Plant Pat. No. 10,772.

*Male or pollen, parent.*—*Weigela florida* cultivar Alexandra, disclosed in U.S. Plant Pat. No. 10,772.

Propagation:

*Type.*—By softwood cuttings.

*Time to initiate roots.*—About 20 days at temperatures of 24° C.

*Time to produce a rooted young plant.*—About two months at temperatures of 24° C.

*Root description.*—Fine, fibrous.

*Rooting habit.*—Freely branching; dense.

Plant description:

*Plant and growth habit.*—Compact and mounding shrub. Vigorous growth habit. Freely branching habit with lateral branches potentially forming at every node.

*Plant height.*—About 37 cm.

*Plant diameter.*—About 40 cm.

Lateral branch description:

*Length.*—About 22 cm.

*Diameter.*—About 3 cm.

*Internode length.*—About 3 cm to 5 cm.

*Strength.*—Strong.

*Texture.*—Pubescent.

*Color.*—Young stems: 183C. Mature stems: 201A to 201D.

Foliage description:

*Arrangement.*—Opposite; simple.

*Length.*—About 5.5 cm.

*Width.*—About 2.8 cm.

*Shape.*—Elliptic to ovate/oblong.

*Apex.*—Acuminate.

*Base.*—Cuneate.

*Margin.*—Serrulate.

*Texture, upper and lower surfaces.*—Smooth, glabrous.

*Venation pattern.*—Pinnate.

*Color.*—Developing foliage, upper and lower surfaces: 187A. Fully expanded foliage, upper surface: 187A; venation, 141D. Fully expanded foliage, lower surface: 185A; venation, 141C.

*Petiole.*—Length: About 3 mm. Diameter: About 2 mm. Texture, upper and lower surfaces: Smooth, glabrous. Color, upper and lower surfaces: 141D.

Flower description:

*Flower arrangement and habit.*—Funnelform flowers arranged in clusters of about three to six flowers. Flowers not persistent. Flowers held mostly outwardly.

*Fragrance.*—None detected.

*Natural flowering season.*—Plants of the new *Weigela* flower from mid-May to early June in Michigan.

*Flower longevity.*—Flowers last about six to eight weeks on the plant.

*Flower diameter.*—About 2 cm to 2.5 cm.

*Flower length (height).*—About 4 cm to 5 cm.

*Flower bud.*—Shape: Ovate to oblong. Length: About 3 cm. Diameter: About 5 mm to 7.5 mm. Color: 61A to 61B.

*Corolla.*—Arrangement: Funnelform, five petals fused into a long tube with separate petal lobes. Petal lobe length: About 5 mm to 8 mm. Petal lobe width: About 1 cm. Petal lobe shape: Orbicular. Petal lobe apex: Rounded. Petal lobe margin: Entire; slightly undulate. Petal texture, upper and lower surfaces: Smooth, glabrous. Color: Petal, when opening, upper surface: 66D. Petal, when opening, lower surface: 61B. Petal, fully opened, upper surface: 66C to 62C. Petal, fully opened, lower surface: 66B to 62C.

*Sepals.*—Quantity per flower: Five. Length: About 8 mm. Width: About 2 mm. Shape: Linear to lanceolate. Apex: Acuminate. Margin: Entire to serrulate. Sepal texture, upper and lower surfaces: Smooth; glabrous. Color, upper and lower surfaces: 59A.

*Peduncles.*—Length: About 2 cm. Angle: About 20° to 30° from stem axis. Strength: Strong; flexible. Texture: Smooth, glabrous. Color: 59A.

*Reproductive organs.*—Stamens: Quantity/arrangement: Five per flower. Anther shape: Oblong. Anther length: About 5 mm. Anther color: 160D. Pollen amount: Moderate. Pollen color: Whitish. Pistils: Quantity: One per flower. Pistil length: About 4 cm. Style length: About 4 cm. Style color: 186C. Stigma color: 160D. Fruits/seeds: Fruit and seed development has not been observed.

Garden performance: Plants of the new *Weigela* have exhibited good tolerance to rain and wind and have been observed to tolerate temperatures from about −10° C. to about 40° C.

Pathogen/pest resistance: Plants of the new *Weigela* have not been observed to be resistant to pests and pathogens common to *Weigela*.

It is claimed:

1. A new and distinct *Weigela* plant named 'Bramwell' as illustrated and described.

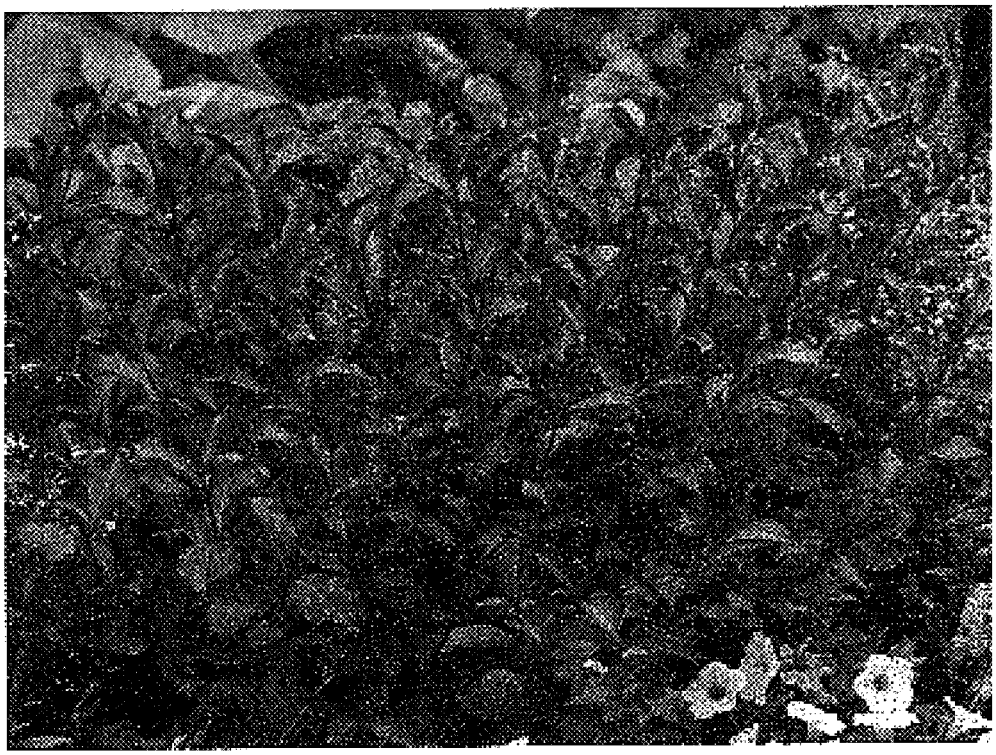
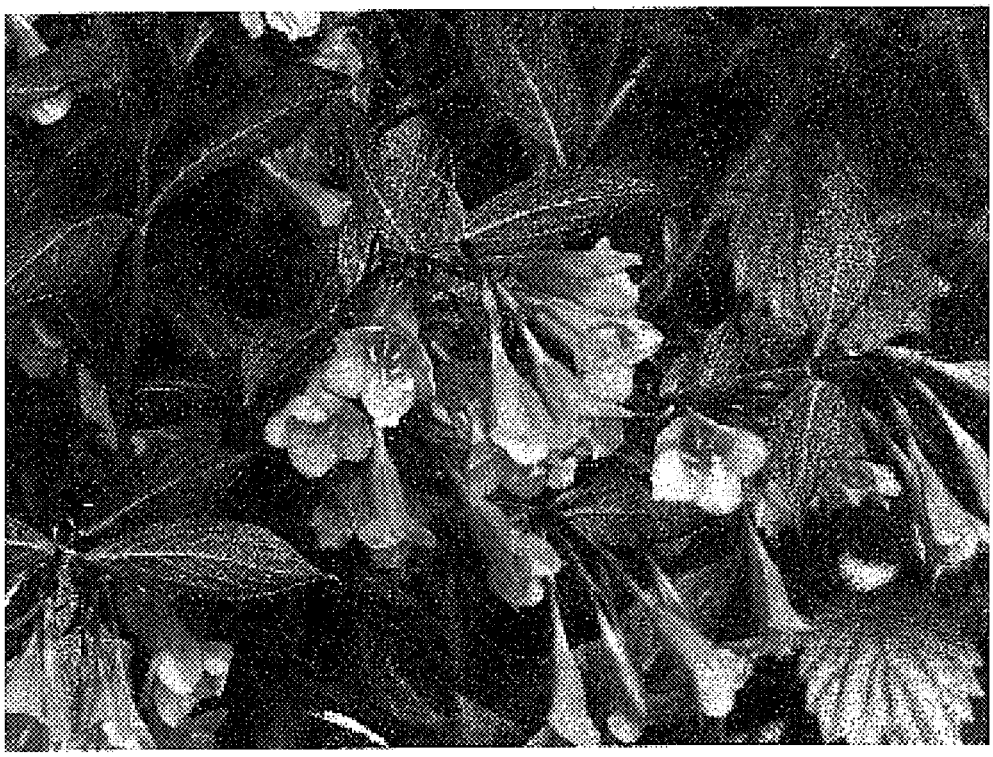

* * * * *